(12) United States Patent
Andersen et al.

(10) Patent No.: US 11,026,860 B2
(45) Date of Patent: Jun. 8, 2021

(54) METHOD AND DEVICE FOR OPTICAL OPHTHALMIC THERAPY

(75) Inventors: Dan E. Andersen, Menlo Park, CA (US); David H. Mordaunt, Los Gatos, CA (US); Michael W. Wiltberger, Santa Clara, CA (US)

(73) Assignee: IRIDEX, Mountain View, CA (US)

( * ) Notice: Subject to any disclaimer, the term of this patent is extended or adjusted under 35 U.S.C. 154(b) by 3151 days.

(21) Appl. No.: 11/170,005

(22) Filed: Jun. 28, 2005

(65) Prior Publication Data

US 2005/0288745 A1 Dec. 29, 2005

Related U.S. Application Data

(60) Provisional application No. 60/583,436, filed on Jun. 28, 2004.

(51) Int. Cl.
*A61H 5/00* (2006.01)
*A61F 9/008* (2006.01)
(Continued)

(52) U.S. Cl.
CPC .......... *A61H 5/00* (2013.01); *A61F 9/00781* (2013.01); *A61F 9/00821* (2013.01); *A61B 3/117* (2013.01);
(Continued)

(58) Field of Classification Search
CPC ...... A61F 9/008–00854; A61F 9/00781; A61F 9/00736; A61F 2009/00868;
(Continued)

(56) References Cited

U.S. PATENT DOCUMENTS 3,703,176 A 11/1972 Vassiliadis et al.
3,883,235 A 5/1975 Lynn et al.
(Continued)

FOREIGN PATENT DOCUMENTS

EP 1354573 * 10/2003 ................ 606/4
EP 1354573 A1 10/2003
(Continued)

OTHER PUBLICATIONS

Naess et al., "Computer-Assisted Laser Photocoagulation of the Retina—a Hybrid Tracking Approach", Journal of Biomedical Optics, Apr. 2002, vol. 7, No. 2, pp. 179-189.
(Continued)

*Primary Examiner* — Amanda K Hulbert
(74) *Attorney, Agent, or Firm* — Dentons US LLP

(57) ABSTRACT

Optical scanning system and method for performing therapy on trabecular meshwork of a patient's eye, including a light source for producing alignment and therapeutic light, a scanning device for deflecting the alignment and therapeutic light to produce an alignment therapeutic patterns of the alignment and therapeutic light, and an ophthalmic lens assembly for placement over a patient's eye that includes a reflective optical element for reflecting the light patterns onto the trabecular meshwork of the patient's eye. The reflective optical element can be a continuous annular mirror (e.g. smooth or with multiple facets) to image the entire trabecular meshwork, or a reflective optical element that moves in coordination with the deflection of the beam. Visualization of the alignment and therapeutic patterns of light on the eye can be implemented by reflection thereof off a visualization mirror that transmits a portion of light emanating from the trabecular meshwork.

50 Claims, 9 Drawing Sheets

(51) Int. Cl.
*A61F 9/007* (2006.01)
*A61B 18/20* (2006.01)
*A61B 18/00* (2006.01)
*A61B 3/117* (2006.01)

(52) U.S. Cl.
CPC .............. *A61B 2018/00636* (2013.01); *A61B 2018/20351* (2017.05); *A61B 2018/20359* (2017.05); *A61B 2018/205545* (2017.05); *A61F 2009/00868* (2013.01)

(58) Field of Classification Search
CPC ......... A61F 9/00821; A61B 17/320708; A61B 17/3211; A61B 2017/320044; A61B 2017/320008; A61B 2018/00636; A61B 2018/20351; A61B 2018/20359; A61B 2018/205545; A61B 3/117; A61H 5/00
USPC .................. 606/4–6, 7, 9–18; 607/88–90
See application file for complete search history.

(56) References Cited

U.S. PATENT DOCUMENTS

| | | | |
|---|---|---|---|
| 4,391,275 A | 7/1983 | Fankhauser et al. | |
| 4,536,065 A | 8/1985 | Sheingorn | |
| 4,685,784 A | 8/1987 | Kirchhuebel | |
| 4,884,884 A | 12/1989 | Reis | |
| 4,901,718 A * | 2/1990 | Bille et al. | 606/4 |
| 4,907,586 A * | 3/1990 | Bille et al. | 606/5 |
| 4,917,486 A | 4/1990 | Raven et al. | |
| 5,144,630 A | 9/1992 | Lin | |
| 5,293,532 A | 3/1994 | Marshall | |
| 5,302,259 A | 4/1994 | Birngruber | |
| 5,336,216 A | 8/1994 | Dewey | |
| 5,347,326 A | 9/1994 | Volk | |
| 5,381,224 A * | 1/1995 | Dixon | G01N 21/6456 250/458.1 |
| 5,391,165 A | 2/1995 | Fountain et al. | |
| 5,425,729 A | 6/1995 | Ishida et al. | |
| 5,480,396 A | 1/1996 | Simon et al. | |
| 5,514,127 A | 5/1996 | Shanks | |
| 5,543,866 A | 8/1996 | Van De Velde | |
| 5,549,596 A | 8/1996 | Latina | |
| 5,568,208 A | 10/1996 | Van De Velde | |
| 5,618,285 A | 4/1997 | Zair | |
| 5,688,264 A | 11/1997 | Ren et al. | |
| 5,743,902 A | 4/1998 | Trost | |
| 5,748,352 A | 5/1998 | Hattori | |
| 5,886,768 A | 3/1999 | Knopp et al. | |
| 5,892,569 A | 4/1999 | Van De Velde | |
| 5,921,981 A | 7/1999 | Baymanyar et al. | |
| 5,943,117 A | 8/1999 | Van De Velde | |
| 5,957,915 A | 9/1999 | Trost | |
| 5,971,978 A | 10/1999 | Mukai | |
| 5,980,513 A | 11/1999 | Frey et al. | |
| 6,011,563 A | 1/2000 | Fournier | |
| 6,033,396 A * | 3/2000 | Huang | A61F 9/008 606/10 |
| 6,059,772 A | 5/2000 | Hsia | |
| 6,066,128 A | 5/2000 | Bahmanyar et al. | |
| 6,096,028 A | 8/2000 | Bahmanyar et al. | |
| 6,099,522 A * | 8/2000 | Knopp et al. | 606/5 |
| 6,149,644 A | 11/2000 | Xie | |
| 6,186,628 B1 | 2/2001 | Van De Velde | |
| 6,267,756 B1 | 7/2001 | Feuerstein et al. | |
| 6,328,733 B1 | 12/2001 | Trost | |
| RE37,504 E | 1/2002 | Lin | |
| 6,347,244 B1 | 1/2002 | Dubnack | |
| 6,494,878 B1 | 12/2002 | Pawlowski et al. | |
| 6,514,241 B1 * | 2/2003 | Hsia et al. | 606/6 |
| 6,607,527 B1 | 8/2003 | Ruiz et al. | |
| 6,620,154 B1 | 9/2003 | Amirkhanian et al. | |
| 6,682,523 B2 | 1/2004 | Shadduck | |
| 6,698,886 B2 | 3/2004 | Pollack et al. | |
| 6,705,726 B2 | 3/2004 | Tanassi et al. | |
| 6,726,679 B1 | 4/2004 | Dick et al. | |
| 6,733,490 B1 | 5/2004 | Falsini et al. | |
| 6,767,098 B2 * | 7/2004 | Erickson | G02B 5/04 351/219 |
| 6,789,900 B2 | 9/2004 | Van De Velde | |
| 6,942,343 B2 | 9/2005 | Farberov | |
| 7,115,120 B2 | 10/2006 | Lin | |
| 7,125,119 B2 | 10/2006 | Farberov | |
| 7,146,983 B1 | 12/2006 | Hohla et al. | |
| 2003/0009155 A1 | 1/2003 | Pawlowski et al. | |
| 2003/0109907 A1 | 6/2003 | Shadduck | |
| 2003/0179344 A1 | 9/2003 | Van de Velde | |
| 2004/0215175 A1 | 10/2004 | Feklistov et al. | |
| 2005/0041200 A1 * | 2/2005 | Rich | A61B 3/117 351/60 |
| 2005/0096639 A1 | 5/2005 | Slatkine et al. | |
| 2005/0143716 A1 | 6/2005 | Vinciguerra et al. | |
| 2005/0159662 A1 | 7/2005 | Imanishi et al. | |
| 2006/0050229 A1 | 3/2006 | Farberow | |
| 2006/0100677 A1 | 5/2006 | Blumenkranz et al. | |
| 2007/0129709 A1 | 6/2007 | Andersen et al. | |

FOREIGN PATENT DOCUMENTS

| | | |
|---|---|---|
| JP | 10-510177 A | 10/1998 |
| JP | 2003532483 | 11/2003 |
| JP | 2004-121814 A | 4/2004 |
| WO | WO 95/27453 | 10/1995 |
| WO | 1996/017555 A1 | 6/1996 |
| WO | WO 00/21475 | 4/2000 |
| WO | WO 0185044 A1 | 11/2001 |
| WO | WO 03/03955 | 5/2003 |
| WO | 2004/027487 A1 | 4/2004 |

OTHER PUBLICATIONS

Markow, M.S. et al., "An Automated Laser System for Eye Surgery", *IEEE Engineering in Medicine & Biology Magazine*, vol. 8, Dec. 1989, pp. 24-29.

Wright, Cameron et al., "Hybrid Approach to Retinal Tracking and Laser Aiming for Photocoagulation", *Journal of Biomedical Optics* 2(2), Apr. 1997, pp. 195-203.

Barrett, Steven et al., "Computer-Aided Retinal Photocoagulation System", *Journal of Biomedical Optics* 1(1), Jan. 1996, pp. 83-91.

Van de Velde, "Role of the Scanning Laser Ophthalmoscope in Photodynamic Therapy of Macular Disease", *Ophthalmic Technologies X, Proceedings of SPIE*, vol. 3908 (2000), pp. 190-201.

Barrett, Steven F. et al., "Digital Imaging-Based Retinal Photocoagulation System", *SPIE*, vol. 2971, pp. 118-128.

Wright, Cameron et al., "Initial In Vivo Results of a Hybrid Retinal Photocoagulation System", *Journal of Biomedical Optics*, vol. 5, No. 1, Jan. 2000, pp. 56-61.

U.S. Appl. No. 12/045,634, filed Mar. 2008, Palankar.

Carlslaw, H.S., Jaeger, J.C., "*Conduction of Heat in Solids*", 2nd ed., Oxford University Press, 1959, pp. 92-132.

Schuele, George, et al., "*RPE Damage Thresholds and Mechanisms for Laser Exposure in the Microsecond-To-Millisecond Time Regimen*", Investigative Ophthalmology & Visual Science, Feb. 2005, vol. 46, No. 2.

European Search Report and Written Opinion dated Mar. 5, 2010 for EP App. No. 08726727.4 filed Mar. 11, 2008, 6 pages.

European Search Report dated Aug. 19, 2009 for EP App. No. 05769199.0 filed Jun. 28, 2005, 3 pages.

International Search Report dated Jul. 14, 2008, for PCT/US2008/003243 filed Mar. 11, 2008, 3 pages.

International Search Report dated Jul. 27, 2007, for PCT/US2006/045957 filed Nov. 30, 2006, 3 pages.

International Search Report dated Jun. 13, 2008, for PCT/US2005/023696 filed Jun. 28, 2005, 3 pages.

International Preliminary Report on Patentability received for PCT Patent Application No. PCT/US2005/023696, dated Feb. 17, 2009, 4 pages.

International Preliminary Report on Patentability received for PCT Patent Application No. PCT/US2006/045957, dated Jun. 3, 2008, 5 pages.

(56) References Cited

OTHER PUBLICATIONS

International Preliminary Report on Patentability received for PCT Patent Application No. PCT/US2008/003243, dated Sep. 15, 2009, 6 pages.
Non Final Office Action received for U.S. Appl. No. 12/045,634, dated Jul. 13, 2011, 33 pages.
Office Action received for Japanese Patent Application No. 2007-518386 dated Oct. 3, 2011, 7 pages ( 3 pages of English translation and 4 pages of Office Action).
Final Office Action received for U.S. Appl. No. 11/606,451 dated Nov. 25, 2011, 7 pages.
Abstract of WO 0185044 A1, publication date Nov. 15, 2001, downloaded from espacenet.com database on Feb. 9, 2010.

* cited by examiner

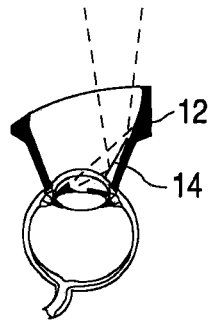
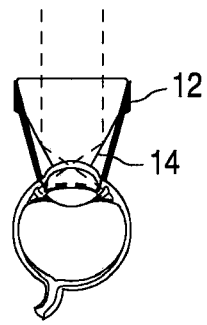
FIG. 3
(PRIOR ART)
FIG. 4
(PRIOR ART)
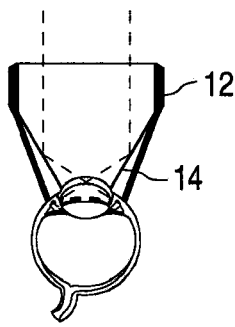
FIG. 5
(PRIOR ART)
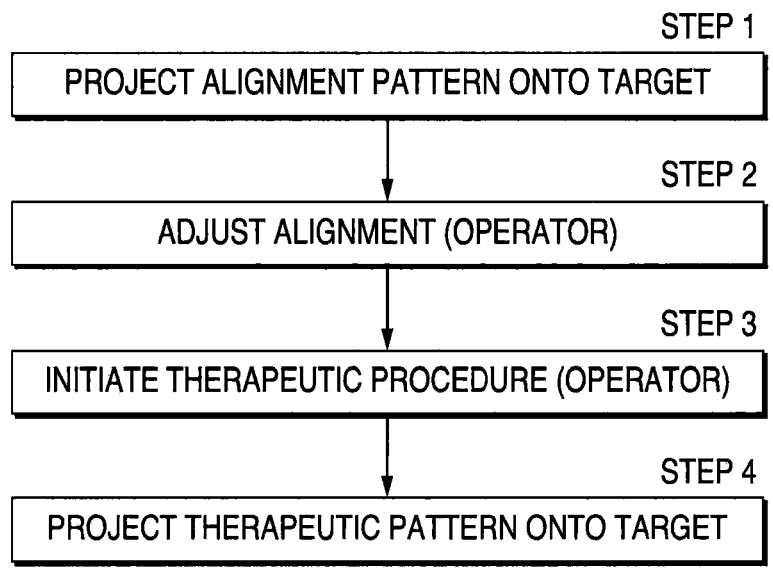
FIG. 6

METHOD AND DEVICE FOR OPTICAL OPHTHALMIC THERAPY

This application claims the benefit of U.S. Provisional Application No. 60/583,436, filed Jun. 28, 2004.

FIELD OF THE INVENTION

The present invention pertains generally to the ophthalmic treatment of a patient's eye, and more particularly to photomedical treatment of the trabecular meshwork of a patient's eye at multiple locations.

BACKGROUND OF THE INVENTION

It is well known that glaucoma is a potentially debilitating group of ophthalmic diseases, each associated with a high risk of blindness. These conditions include, but are not limited to: open-angle glaucoma, exfoliation glaucoma, and pigmentary glaucoma. Common to all of these glaucoma conditions is the inability of the trabecular meshwork (TM) to sufficiently balance the creation of aqueous humor from the ciliary body with its removal, thereby elevating intraocular pressure (IOP). The ocular hypertension associated with glaucoma causes a gradual degeneration of cells that make up the optic nerve. As nerve cells die, vision is slowly lost. Often, the loss of vision is unnoticeable until significant nerve damage has occurred.

Loss of vision from glaucoma is irreversible. Recent prevalence figures from the National Institutes of Health and the World Health Organization regarding glaucoma are chilling. Glaucoma is the second leading cause of blindness in the U.S. and the first leading cause of preventable blindness. It is estimated that over 3 million Americans have glaucoma, but only half of them know they have it, most suffering from what is known as open angle glaucoma. Approximately 120,000 of those people are blind from glaucoma, accounting for 9%-12% of all cases of blindness. Glaucoma accounts for over 7 million visits to U.S. physicians each year. In terms of Social Security benefits, lost income tax revenues, and health care expenditures, the annual cost to the U.S. government alone is estimated to be over $1.5 billion. The worldwide number of suspected cases of glaucoma is around 65 million. Although glaucoma as such cannot be prevented, its consequences can be avoided if the disease is detected and treated early.

Today there are a variety of therapeutic options available for treating glaucoma. Invasive surgical intervention is typically used as a last resort. Front-line therapy is the use of drugs to lower IOP. These are, of course, not panacea. In fact, drugs don't work for many patients. The preponderance of these open angle glaucoma cases is presently addressed by laser therapies, such as Argon Laser Trabeculoplasty (ALT) and Selective Laser Trabeculoplasty (SLT). Both ALT and SLT procedures require the even spacing of approximately 100 laser spots per 180 degrees of a patient's trabecular meshwork (TM). Spot diameters of 50 μm and 400 μm are typical for ALT and SLT, respectively. ALT treatments usually involve only 180 degrees of a patient's trabecular meshwork (TM), while SLT is delivered to the entire circumference for a total of 200 spots. Both of these therapies are tedious and time consuming for doctor and patient, as the laser treatment spots are applied manually and sequentially. The main difference between SLT and ALT, however, is the pulse duration of the therapeutic light. SLT uses short pulses to substantially spatially confine the heat produced to the targeted melanin particles, which is why SLT is considered to be "selective" or "sub-threshold" therapy, while ALT uses longer pulses causing damage to the TM itself, and is known as standard, or "coagulative" therapy. Both ALT and SLT treat the TM with light that is predominantly absorbed by the melanin residing therein.

The optical absorption spectra of melanin, oxy-hemoglobin (HbO2), and deoxy-hemoglobin (Hb), the predominant intraocular chromophores, are shown in FIG. 1. The structure of this ocular anatomy is shown in FIG. 2, and includes a cornea 1, an iris 2, an anterior chamber 3, a pupil 4, a lens 5, a cillary body 6, trabecular meshwork TM 7, conjunctiva 8, sciera 9, and an angle 10. The fluid flow is shown by the arrows in FIG. 2. As can be seen from this figure, optical treatment of the TM would require light entering the eye at a very shallow entry angle.

In U.S. Pat. No. 5,549,596, Latina discloses a method for the selective damaging of intraocular pigmented cells which involves the use of laser irradiation, while sparing nonpigmented cells and collagenous structures within the irradiated area. This method is useful for the treatment of glaucoma (SLT), intraocular melanoma, and macular edema. Latina discloses the basic method of selective therapy using pulsed lasers. However, this delivery of individual pulses is tedious and time consuming.

In U.S. Pat. Nos. 6,059,772 and 6,514,241, Hsia, et al disclose a non-invasive apparatus and method for treating open angle glaucoma in a human eye by thermally ablating a targeted region of the TM using pulsed radiation having a wavelength between 350-1300 nm, energy of 10-500 mJ, and pulse duration of 0.1-50 μs. Here pulses slightly longer than those employed with SLT are used. However, Hsia et al. don't address the tedious and time consuming effects of delivering individual pulses.

In U.S. Pat. No. 6,682,523, Shadduck discloses a system for non-invasive treatment of a patient's trabecular meshwork to treat glaucoma. The system and technique applies energy directly to media within clogged spaces in a patient's TM to increase aqueous outflow through the laser irradiation of microimplantable bodies (nanocrystalline particles) carrying an exogenous chromophore which are placed in the deeper regions of the TM. This causes thermoelastically induced microcavitation that serves to ablate the debris and accumulations therein. This approach is similar to that of Latina in that it requires the use of short pulses, and so should be considered as "selective" therapy. Unlike Latina, however, it makes use of an exogenous chromophore. The choice of wavelength for the treatment light source is no longer dependent upon melanin absorption, but instead will be primarily concerned with the absorption of this exogenous chromophore. However, Shadduck also fails to address the tedious and time consuming effects of delivering individual pulses.

FIGS. 3-5 show increasingly more complex versions of currently available gonioscopic lens assemblies 12 used to access the TM. Such lens assemblies are presently required to redirect light into the eye at very shallow entry angles so the light will reach the TM. In addition to one or more focusing lenses, all of these lens assemblies 12 include mirrors 14 to reflect the light into the eye at shallow entry angles. FIG. 3 shows a single mirror design, FIG. 4 shows a 2-mirror design, and FIG. 5 shows a 4-mirror design. In each case, the mirrors used are planar. The multiple mirrors are discontinuous and separated from one another, thus creating gaps in the field of view. Thus, these gonioscopic lenses must be moved during the procedure to fill the gaps caused by the discontinuous mirrors, as well as to access portions of the TM outside of the relatively small field of view.

Accordingly, there is a need for simple and flexible multi-location treatment of the trabecular meshwork of a patient.

SUMMARY OF THE INVENTION

The present invention solves the aforementioned problems by providing an optical scanning system for performing therapy on target eye tissue of a patient. The system includes a light source for producing a beam of light, a scanning device for deflecting the beam of light to produce a pattern of the light beam, and an ophthalmic lens assembly having a contact surface for contacting the patient and having a reflective optical element for reflecting the light beam pattern onto the target eye tissue.

In another aspect of the present invention, an optical scanning system for performing therapy on trabecular meshwork of a patient's eye includes a light source for producing a beam of light, a scanning device for deflecting the beam of light to produce a pattern of the light beam, and an ophthalmic lens assembly for placement over a patient's eye and including a reflective optical element for reflecting the light pattern onto the trabecular meshwork of the patient's eye.

In yet one more aspect of the present invention, a method of performing therapy on trabecular meshwork of a patient's eye includes placing an ophthalmic lens assembly over the patient's eye, wherein the ophthalmic lens assembly includes a reflective optical element, producing a beam of light, deflecting the beam of light to produce a pattern of the light beam, and reflecting the light pattern off of the reflective optical element and onto the trabecular meshwork of the patient's eye.

Other objects and features of the present invention will become apparent by a review of the specification, claims and appended figures.

BRIEF DESCRIPTION OF THE DRAWINGS

FIGS. 3-5 are side cross-sectional views of prior art gonioscopic lens assemblies.

FIG. 6 is a flow diagram of a method of the present invention.

DETAILED DESCRIPTION OF THE PREFERRED EMBODIMENTS

Figure 1:
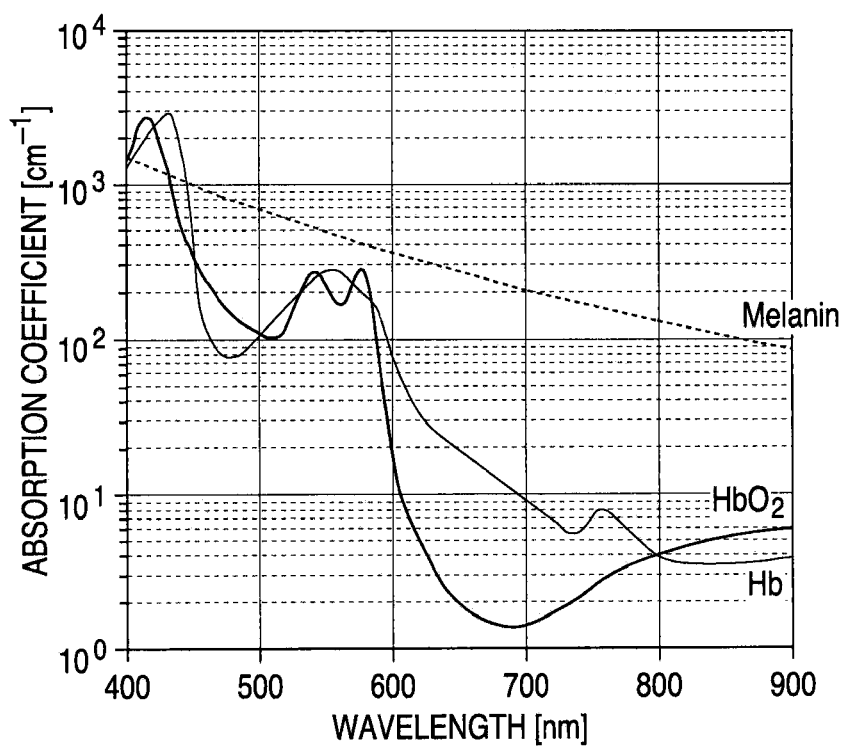
FIG. 1 is a graph showing the optical absorption spectra of the predominant ocular chromophores, namely melanin, oxy-hemoglobin (HbO2), and deoxy-hemoglobin (Hb).
Figure 2:
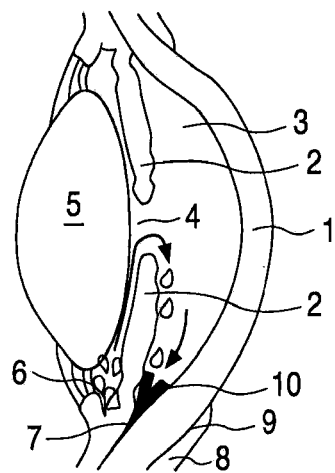
FIG. 2 is a side cross-sectional view of the anatomy of a human eye's anterior chamber, including the trabecular mesh (TM).
Figure 7A:
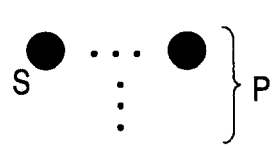
FIGS. 7A-7D illustrate exemplary scan patterns for use with a pulsed or gated light source.
Figure 7B:
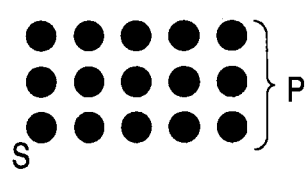

The present invention provides both instruments and methods for treating the trabecular meshwork (TM) of a patient's eye utilizing scanning optical systems. FIG. 6 is a flow diagram of a method of the present invention. In step 1, a visible alignment pattern is projected onto the TM. This alignment pattern coincides with the portions of the eye that will later be illuminated with therapeutic light, and ensures the system is properly aligned to the target portion(s) of the TM. In step 2, the user may manually adjust the alignment pattern. This step is optional, depending upon the accuracy of the original projection. Such adjustments may involve adjusting the size, scale, shape, rotation, curvature, ellipticity, etc. of the pattern and/or the spots that form the pattern to match the requirements of the particular patient contact lens used. In step 3, an initiation of the therapeutic procedure is triggered by the operator, such as by pressing a foot switch, or finger switch, etc. The fourth step is to automatically deliver (in response to the operator action of step 3) therapeutic pattern of light to the TM, which is substantially aligned to the alignment pattern of light. Therapeutic light can be for diagnosis and/or treatment purposes.

The alignment and therapeutic patterns may be comprised of a single spot of light, multiple spots of light, a continuous pattern of light, multiple continuous patterns of light, and/or any combination of these. In addition, the alignment pattern need not be identical to the therapeutic pattern, but preferably at least defines its boundaries in order to assure that the therapeutic light is delivered only within the desired target area for patient safety. This may be done, for example, by having the alignment pattern provide an outline of the intended therapeutic pattern. This way the spatial extent of the therapeutic pattern may be made known to the user, if not the exact locations of the individual spots themselves, and the scanning thus optimized for speed, efficiency and accuracy. The alignment pattern may also be made to be perceived as blinking in order to further enhance its visibility to the user.

The method and apparatus of the present invention can utilize either or both continuous wave (CW) and pulsed light sources, for standard, selective, and/or sub-threshold therapies. The preferential optical absorption and subsequent heating characteristics of selective therapies ameliorate the possibility of causing damage to tissues and/or structures adjacent to the trabecular meshwork. Therefore, such selective therapies also allow for the possible irradiation of adjacent tissues and/or structures without the risk of substantial collateral damage. With that in mind, the alignment and therapeutic patterns may involve adjacent tissues and/or structures while being predominantly disposed to the trabecular meshwork during such selective therapies. For the sake of brevity, the apparatus and method of the present invention are described with respect to the trabecular meshwork as being the target tissue, however it should be understood that adjacent tissues and/or other tissue may be involved during such selective therapies.

Preferably, the therapeutic pattern is completed in approximately less than one second, as that is a typical reliable patient fixation time. Longer exposure times increase the risk that the patient's eye may inadvertently move. Therefore, it is preferable that the therapy be completed by a single operator action once the system is aligned to the targeted tissue. The present invention provides reduced treatment times for laser trabeculoplasty procedures by projecting a pattern of therapeutic light that can treat large portions if not all of the TM in a single system exposure. With the therapeutic pattern being delivered in approximately less than one second, the eye can be considered motionless, and thus the present invention provides for increased patient comfort and decreased treatment times over standard laser trabeculoplasty procedures.

The alignment and therapeutic patterns are preferably formed as a pattern P of spots S of light projected onto the target tissue, as illustrated in FIGS. 7A-7D. The patterns can be specially tailored for the tissue being treated, and/or for the delivery optics (such as the particular gonioscopic lens assembly used to deliver the alignment and therapeutic light). Spots S are shown as round, but need not be. Spots S will likely, but need not, have a characteristic intensity profile, such as Gaussian or top-hat distributions, that are characteristic of the light source. Preferably, the all the spots S in the alignment or therapeutic patterns are delivered in a single system exposure. For example, with a pulsed light source, the entire pattern P is delivered in one user activated system exposure, with each light source pulse producing a separate spot S.

Figure 7D:
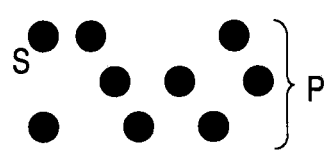

Pulses for current therapies utilize pulse durations which are on the order of nanoseconds to microseconds. Thus, either spots S would not move during the pulse, or, given these short pulse durations, any scanned motion would likely be minimal (i.e. the scanner forming pattern P may be made to move continuously while the light is pulsed and still not compromise the therapy). Of course, other pulse durations are possible. When the pulse duration becomes long enough that the scanner would cause appreciable and unwanted movement during the delivery of a spot S, the scanner could be made to dwell at that location during irradiation. A multitude of spots S may thus be assembled to create one or two dimensional patterns P as shown in FIGS. 7A-7D. Pattern P need not form a regular array of spots S, as illustrated in FIG. 7D. When used with a multiple mirror gonioscopic lens assembly, the number of patterns P created may match the number and positioning of gonioscopic lens mirrors. The angular and spatial extent of spots S and pattern P may be limited by the specifics of the gonioscopic lens assembly used. Specifically, the gonioscopic mirror(s) may ultimately dictate the attainable extent of the pattern P and its elements.

Figure 8A:
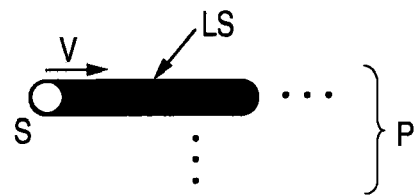
FIGS. 8A-8D illustrate exemplary scan patterns for use with a continuous wave (CW) light source.
Figure 8B:
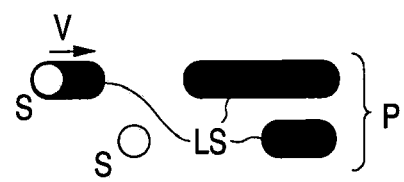
Figure 7C:
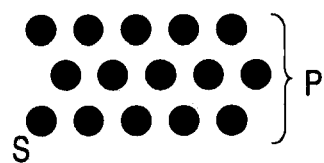
Figure 8C:
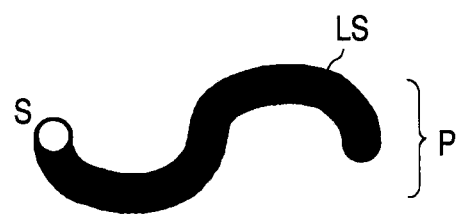
Figure 8D:
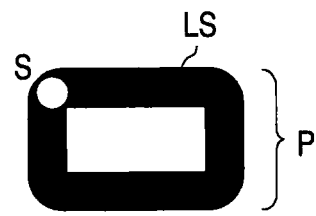

FIGS. 8A-8D illustrate how one or more spots S can be used to trace out or even form elongated straight or curved line segments to form patterns P, which is ideal for continuous wave (CW) light sources. For example, in FIG. 8A, spot S is scanned at a velocity V to form line segment scans LS of pattern P. Each line segment LS terminates when the light source is no longer delivering light to the spot S being scanned that forms the line segment LS. This may be done in many ways, such as, gating the light source on-and-off directly, using a shutter placed in the optical path, by use of an aperture, etc. As shown in FIG. 8B, a pattern P may be formed of a plurality of line segments LS and/or spots S. The line segment LS may be shaped or curved, as illustrated in FIG. 8C, or even curved/shaped to form geometric objects or symbols as illustrated in FIG. 8D (which is particularly suited as an outline of the target tissue for the alignment pattern as previously discussed).

Thus, for the purposes of this disclosure, a "pattern" of light shall mean at least two spots S that do not completely overlap (or do not overlap at all), or one or more spots that move during a single pulse or with cw light resulting in a projected straight or curved line segment.

As discussed in more detail below, delivering a single, continuous scan to irradiate 360 degrees around the TM is possible given a continuous gonioscopic mirror. It is important to note that by knowing the size, orientation, and energy distribution of the fundamental spot S, a particular dosimetry may be specified by adjusting not only the optical power or spot dimensions, but also the scan velocity V. In this manner, light may be made to dwell on a point of the trabecular meshwork TM for a specified time, thus delivering a specific amount of energy at that point. In this way, the dwell time may be considered to be the "pulse duration" of the CW light. With that in mind, a practical example using a pulse duration of 1 µs, a round spot S with a diameter of 100 µm, requires a scanning velocity of 100 µm per µs at or about the target area. Knowing that the trabecular meshwork TM has an average diameter of roughly 20 mm, this means that the entire internal circumference of the trabecular meshwork TM can be scanned in only 300 µs.

Figure 9:
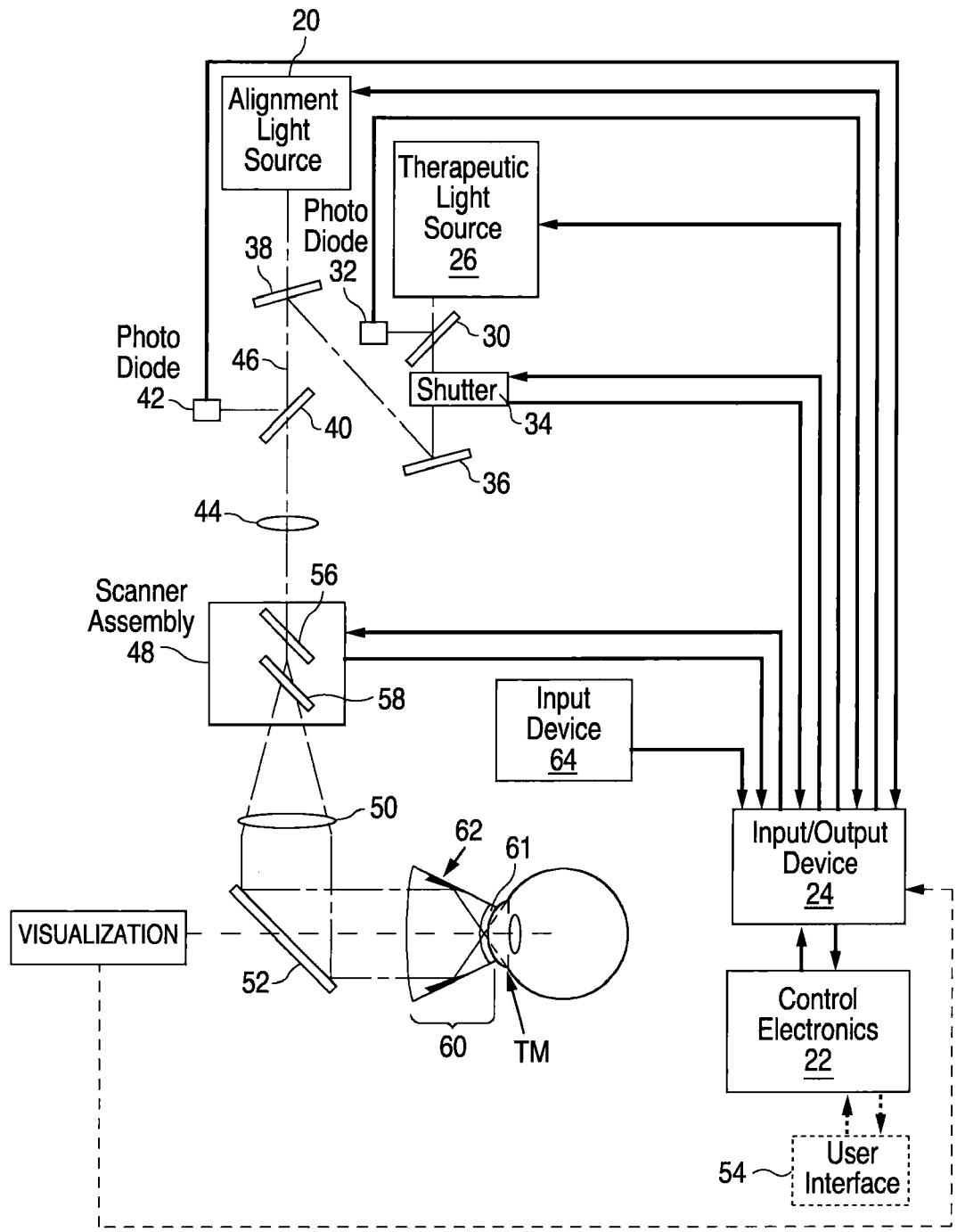
FIG. 9 is a schematic diagram illustrating the light generation and scanner assembly of the present invention.

FIG. 9 is a schematic diagram of a system suitable for performing the method of FIG. 6. The alignment light is created using an alignment light source 20, which may be controlled by control electronics 22 via an input/output device 24. Likewise, the therapeutic light can be created using the therapeutic light source 26. Light sources 20 and 26 can be any gas or solid state laser device, or even light emitting diodes. Light sources 20/26 are preferably separate devices because they usually produce light at different wavelengths and power levels, however, they could be combined into a single light source that produces alignment and therapeutic light with differing or identical wavelengths. Alignment light from source 20 preferably is visible to the eye (however, if an alternate visualization scheme such as infrared imaging is employed, it may be non-visible). Therapeutic light from source 26 may also be visible, but need not be. As can be seen in FIG. 1, the optical absorption of the target chromophore and melanin is extremely broad. Furthermore, if the targeted chromophore is exogenous, its absorption properties will primarily dictate the choice of wavelength for therapeutic light source 26. If therapeutic light source 26 does produce visible light, it may be also used for producing the alignment pattern instead of alignment light source 20 (e.g. by simply reducing its output power during system alignment when no eye safety filters are in the visualization pathway). Likewise, if therapeutic light source 26 produces non-visible light, it may be used for alignment in a similar manner with a non-visible imaging scheme (e.g. by using an infrared camera, a scanning laser ophthalmoscope, etc.).

Light output from therapeutic light source 26 first encounters a mirror 30 which reflects a fixed portion of the therapeutic light to a photodiode 32 to measure its power for safety purposes. The therapeutic light then encounters shutter 34, mirror 36, and mirror 38. Shutter 34 fundamentally serves to control the delivery of the therapeutic light, and can be used to rapidly gate and/or generally block the therapeutic light. Mirror 36 is an optional turning mirror, and mirror 38 is used to combine the therapeutic light with the alignment light from light source 20 to form combined alignment/therapeutic light beam 46, where alignment light from source 20 may be adjusted so that it is coincident with the therapeutic light downstream. It should be noted that the alignment light and the therapeutic light need not be produced simultaneously, and in that case mirror 36 in actuality combines beam paths for these two beams of light (i.e. alignment/therapeutic light 46 contains only alignment light at certain times and therapeutic light at other times). A mirror 40 is used to reflect a portion of the combined alignment and therapeutic light into photodiode 42 for additional measurement (and also provides redundant monitoring of the state of shutter 34).

A lens 44 can be used to condition the combined alignment/therapeutic light 46 prior to its entry into a scanner assembly 48. Lens 44 may be a single lens, or a compound lens. If lens 44 is a compound lens, it may be configured as a zoom lens assembly that adjusts the size of spots S, and therefore, pattern P. Another lens 50 can be placed one focal length away from the optical midpoint of the scanner assembly 48 to produce a telecentric scan (however this is optional). For systems including lens 50, a telecentric scan serves to maximize the scan speed, so long as the remaining optical elements are large enough to contain the entire scan. Most of the current available ophthalmic contact lenses demand telecentric input.

Light 46 next encounters mirror 52, which reflects the light toward the target. Mirror 52 includes a high reflective coating that spectrally matches the outputs of the alignment and therapeutic light, yet allows visualization light coming from the target to pass through so that target area can be visualized through mirror 52. Preferably, the coating would be constructed to white balance the transmission through mirror 52, where the coating is more complicated and makes the colors appear more natural instead of a pinkish result when using a green notch filter coating. Lens 50 may also be used to image the optical midpoint of the scanner assembly 48 onto mirror 52, to minimize the size of the mirror 52 in an attempt to increase the overall solid angle subtended by the visualization device. When mirror 52 is small, it may be placed directly in the visualization path without much disturbance. Mirror 52 may also be placed in the center of a binocular imaging apparatus, such as a Zeiss slitlamp biomicroscope, without disturbing the visualization. Visualization may be accomplished by directly viewing the retina through mirror 52, or by creating a video image from the light passing through mirror 52 to be displayed on a remote monitor or a graphical user interface 54 as shown in FIG. 9.

Scanning assembly 48 preferably includes two optical elements 56 and 58 (e.g. mirrors, lenses, diffractive elements, rotating wedges, etc.), that can be individually tilted or moved in an orthogonal manner to deviate (deflect) the optical beam 46, and ultimately direct it towards the trabecular meshwork TM, where it is to be finally disposed in a manner forming patterns P thereon. For example, optical elements 56/58 can be mirrors mounted to galvanometers, solenoids, piezoelectric actuators, motors, servos, motors or other type of actuators for deflecting the beam 46 by tilting the mirrors. Of course, single element 2 dimensional scanners may also be used, such as acousto-optic deflectors, optical phased arrays, or micro mirror devices. Alternately, the mirrors could have optical power (e.g. have surface curvature), where deflecting the beam can be accomplished by translating the mirrors. Or, optical elements 56/58 could be lenses, which deflect the beam by translational movement of the lenses. Other techniques of scanning light beam 46 without scanner assembly 48 include moving the light sources 20/34 themselves directly, and using a single moving optical element (including moving mirror 52). If optical elements 56/58 have optical power, then compensating optical elements (not shown) may be added to produce an image, as opposed to a simple illumination, on the trabecular meshwork TM.

The light beam 46 scanned by scanner apparatus 48 and reflected by mirror 52 is focused onto the trabecular meshwork by an ophthalmic lens assembly 60 that includes gonioscopic mirror(s) 62 that reflect the light 46 into the eye at very shallow angles. Ophthalmic lens assembly may also include one or more lenses, such as contact lens 61 that is placed directly on the eye. For better positioning, the Ophthalmic lens assembly 60 includes a contact surface (e.g. surface of contact lens 61, surface on nose bridge, surface on forehead member, etc.) that contacts the patient and holds the assembly 60 steady relative to the patient and in particular to the patient's eye. Ophthalmic lens assemblies with 1, 2 and 4 gonioscopic mirrors are well known, and fail to provide uninterrupted views of the TM. Therefore, it is preferable that the gonioscopic mirror 62 is continuous, as described below in further detail with respect to FIGS. 11 and 12.

The position and character of pattern P may be further controlled by use of a joystick or other similar input device 64. Pattern P may also be rotationally aligned to the gonioscopic mirror(s) 62 by simply rotating ophthalmic lens assembly 60. The ultimate disposition of pattern P is only limited by the optics of the system, and, of course, any patient idiosyncrasies which might serve to perturb it. Ophthalmic lens assembly 60 may be a contact or non-contact type assembly (e.g. having an optical element that touches or does not touch the patient's eye).

Light source 20 may be gated on and off by commands from control electronics 22 via input and output device 24 to produce discrete spots, or simply run CW to create continuous scans as a means to produce a pattern P of alignment light. Electronics 22 likewise controls the position of scanning optics 56/58, and therefore ultimately that of pattern P of therapeutic light, as discussed above with respect to FIGS. 7A-7D and 8A-8D. In this way, pattern P, or any of its elements may be made to be perceived by the user as blinking. Furthermore, the perception of both discrete spots and blinking may be accomplished by simply scanning quickly between elements of pattern P so as to limit the amount of light registered by the user in those intermediate spaces.

As disclosed, the present invention is suitable for use with pulsed or CW light sources. Likewise, its inherent flexibility allows the use of CW light sources where currently only pulsed light sources are used, such as ALT and SLT. It may do so by limiting the dwell time of the scanned light on the target tissue, allowing for the tissue to experience a "pulse" of light even though the source itself has not actually been pulsed. Adjustment of the size of spot S, the scan velocity V, and thereby the dwell time on tissue, allows for an infinite range of exposure possibilities which are bounded only by the speed of the scanning elements.

Figure 10:
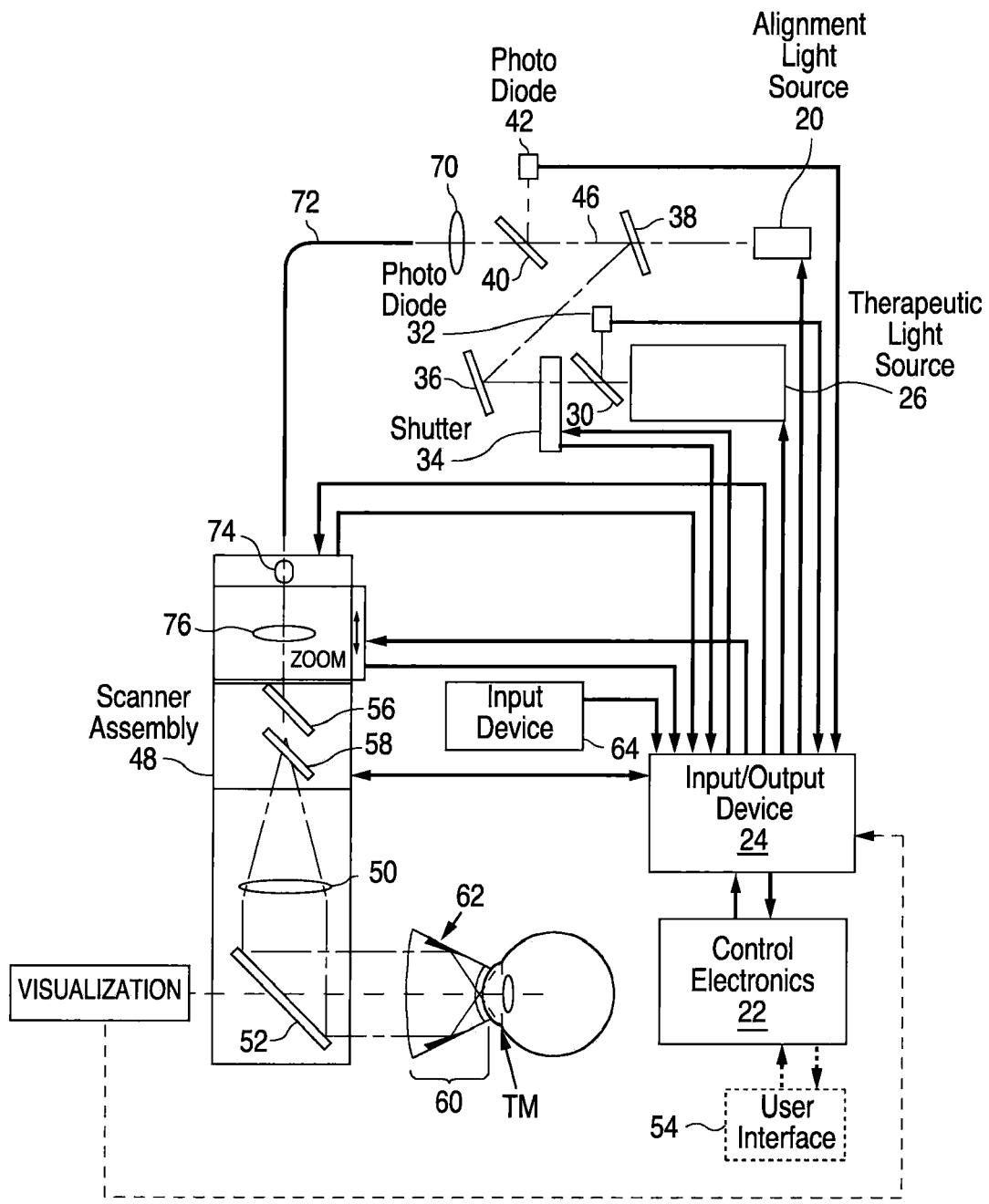
FIG. 10 is a schematic diagram illustrating the light generation and scanner assembly of the present invention, utilizing fiber optic delivery.

FIG. 10 shows a schematic diagram of an alternate embodiment to the system of FIG. 9, with optical fiber delivery. In this embodiment, lens 70 is used to inject the combined alignment and therapeutic light 46 into an optical fiber 72. Light 46 exiting optical fiber 72 encounters lenses 74 and 76 which condition the light and can act as a zoom system before the light enters the scanner assembly 48. An image of the output face of optical fiber 72 may be relayed to the target area, and a "flat-top" intensity profile used, rather than the typical Gaussian profile. The remainder of the system of FIG. 10 is the same as that shown in FIG. 9.

Figure 11:
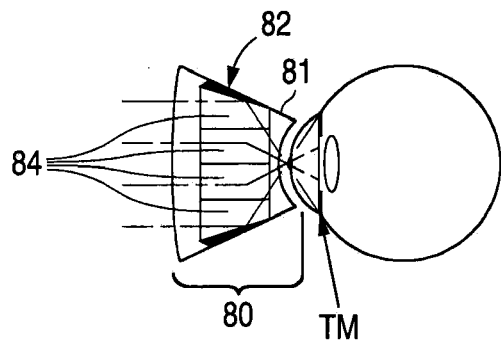
FIG. 11 is a side cross-sectional view of a gonioscopic lens assembly of the present invention, optimized for scanning therapy.
Figure 12:
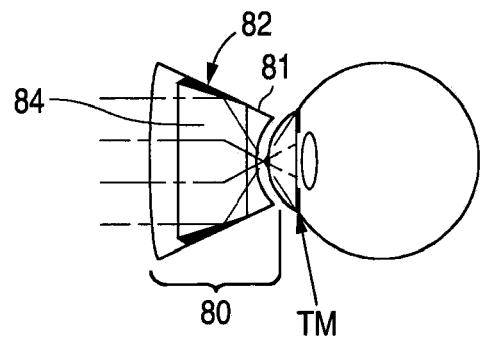
FIG. 12 is a side cross-sectional view of an alternate embodiment of the gonioscopic lens assembly of the present invention, optimized for scanning therapy.

FIGS. 11 and 12 illustrate an ophthalmic lens assembly 80 optimized for scanning alignment and therapeutic patterns onto the TM. Lens assembly 80 can include one or more lenses for focusing the light 46 into the eye, such as a lens 81. Lens assembly 80 also includes a continuous annular internal gonioscopic mirror 82, which "sees" the entire circumference of the trabecular meshwork TM, and thus allows for a single complete treatment of the entire TM without having to move or reposition lens assembly 80. A continuous annular mirror means either a single continuously formed annular mirror (i.e. FIG. 12), or a mirror formed of a plurality of facets 84 that are abutted together so that there are no breaks or gaps in entire circumference of the mirror (i.e. FIG. 11). Thus, while there might be slight discontinuities in the image caused by junctions of mirror facets, there are no gaps in which light is lost as it is scanned around the circumference of the gonioscopic mirror 82. In this way, a complete 360 degree scan of the trabecular meshwork TM may be made that is more complete and uniform than can be made with present gonioscopic lenses having mirror faces separated from each other. The number of gonioscopic mirror facets can be chosen so as to provide for substantially homogeneous treatment throughout such a complete scan. A contiguous multi-facet gonioscopic mirror 82 is illustrated in FIG. 11, having 10 planar facets 84 abutted together. A continuous, circularly symmetric internal gonioscopic mirror 82 is illustrated in FIG. 12. Such a mirror maybe frusto-conical, as shown. While its symmetry obviates the need to match the angular and spatial extents of the scanner output to produce a uniform scan, such a gonioscopic mirror 82 may require anamorphic optical compensation to offset the asymmetry of its focusing. To this end, the optical components of ophthalmic lens assembly 80 maybe made to incorporate sphero-cylindrical, or toroidal focusing to counteract the effects of the gonioscopic mirror 82. It should be noted that other optical elements, instead of mirror 82, such as diffractive or refractive element(s), can be used to direct the light 46 into the eye and onto the TM (in a continuous manner), for example prisms, gratings, etc. Similarly, an aspheric optical element may be added to the scanner assembly itself rather than the contact lens, and made to rotate in coordination with position of the scanned light to produce the desired optical homogeneity, as is discussed in more detail below.

The scanning system used in conjunction with the lens assemblies of FIGS. 11 and 12 may be made to provide scans of alignment and/or therapeutic light whose angular and spatial extents match the particular optics of the ophthalmic lens assembly 80, so as to produce scans with overall uniformity in the trabecular meshwork TM. For example, the scans by scanning assembly 48 can be adjusted to compensate for the number, locations and angular orientations of multiple mirror facets 84 to produce uniform scans of the TM off of those mirror facets 84. Such scans are preferably preprogrammed into the control electronics 22, and/or adjusted by the user, so that automated treatment can occur once the system is aligned to the TM and the user triggers a therapeutic scan.

Figure 13:
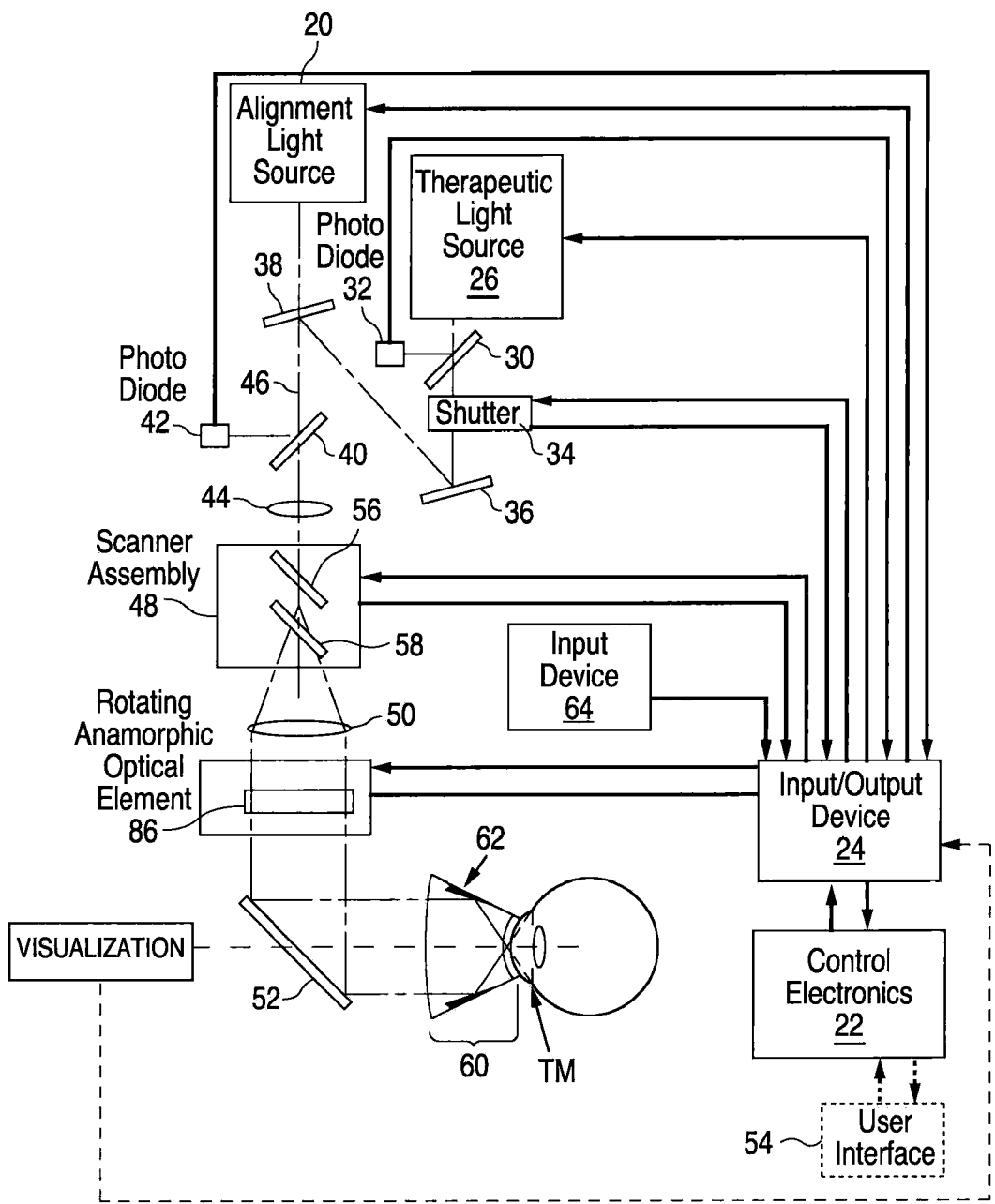
FIG. 13 is a schematic diagram illustrating an alternate embodiment of the light generation and scanner assembly of the present invention.

FIG. 13 illustrates a schematic diagram of another embodiment similar to that shown in FIG. 9, except with the addition of a rotating anamorphic optical element 86. In this embodiment, anamorphic optical element 86 is used to compensate for the cylindrical focusing of an ophthalmic lens assembly as shown in FIG. 12. Control electronics 22 coordinates the position of scanning mirrors 56/58, and the rotation of anamorphic optical element 86 to ultimately produce a scan with the desired optical homogeneity disposed at the trabecular meshwork TM. Anamorphic compensation may be provided in a variety of ways. Anamorphic optical element 86 may be, for example, a cylindrical lens (either single or multi element). Such a lens need not be a single element lens, but may be a multi-element lens. A multi-element lens may serve to better compensate for any chromatic aberrations which may cause differences between the alignment light and the therapeutic light when their optical outputs are different wavelengths. This, however, comes at the cost of increased size and mass of the compensating anamorphic optical element 86, thereby increasing its moment of inertia and making it more difficult to accelerate quickly. A mirror maybe used as anamorphic optical element 86 to eliminate the need for such design complexities. Furthermore, anamorphic optical element 86 may be an adaptive optic, which would then not need rotation. Instead, it can be reconfigured to produce the desired effects.

Figure 14:
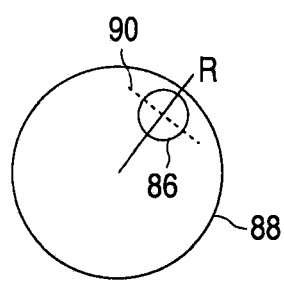
FIG. 14 is a top view of an anamorphic optical element on an eccentric mount according to the present invention.

FIG. 14 illustrates how to ameliorate the difficulties of accelerating anamorphic element 86 described above. Here the lateral dimensions of anamorphic element 86 have been minimized such that it just accommodates the output of the scanner assembly 48. Anamorphic element 86 may then be placed into an eccentric mount 88 so that it will capture the light 46 as eccentric mount 88 rotates in coordination with the scan. The optical axis 90 of anamorphic element 86 is substantially aligned perpendicular to the radius R of eccentric mount 88 in order to be complementary to the optical effects of the ophthalmic lens assembly 80 discussed above. This assembly now constitutes a configuration of anamorphic element 86 which may be accelerated more simply due to its having a moment of inertia that is significantly reduced as compared to a configuration of anamorphic element 86 that is composed predominantly of optical elements. In this way, a substantially uniform spot may be produced at any point in the trabecular meshwork TM. Subsequently, this provides for the uniform scanning of both pulsed and cw light sources. In the case of CW light sources, the scan speed may be controlled to allow for the adjustment of the dwell time and accumulated energy deposition of the light, as discussed above with respect to FIGS. 8A-8D.

Figure 15:
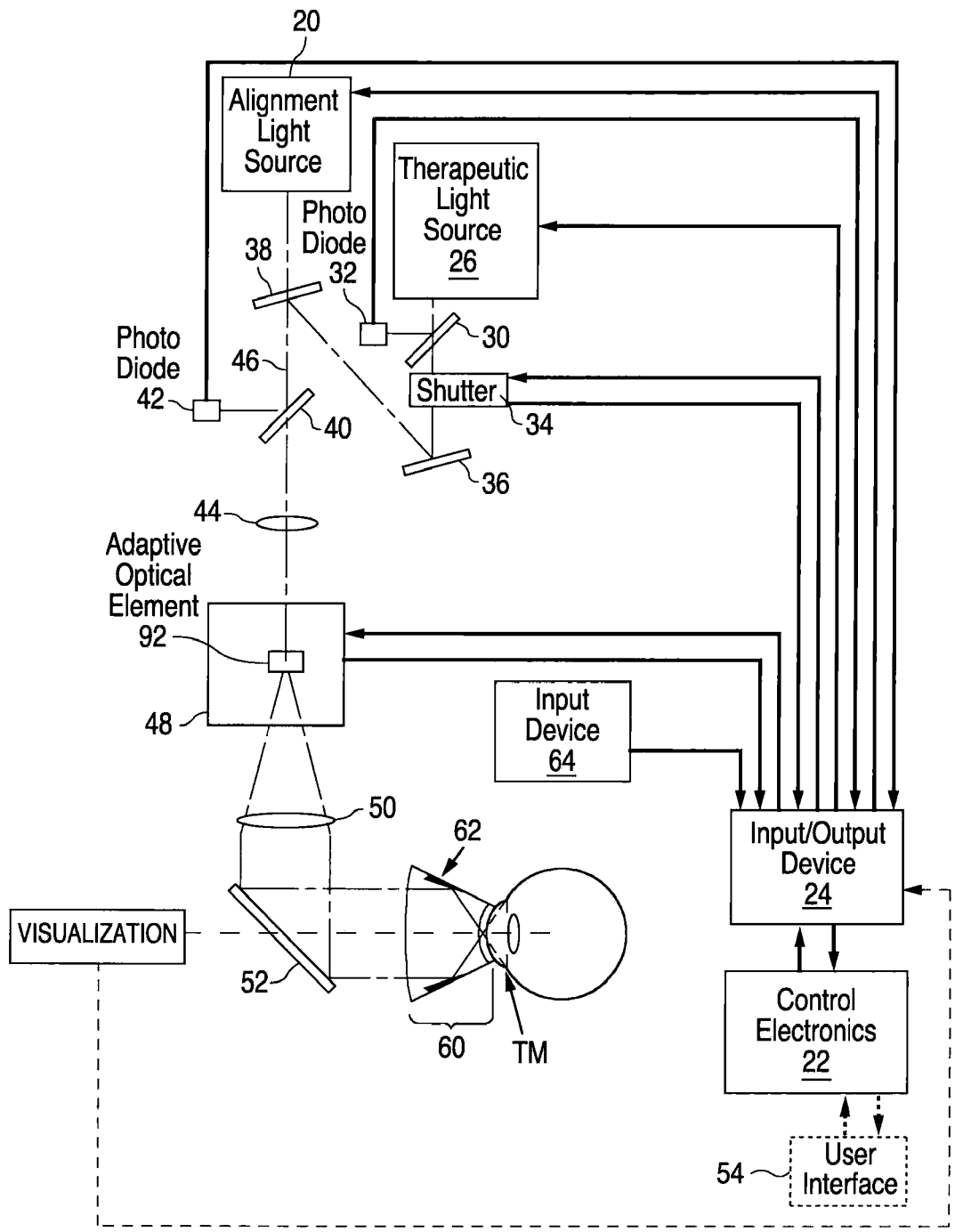
FIG. 15 is a schematic diagram illustrating another alternate embodiment of the light generation and scanner assembly of the present invention.

FIG. 15 shows a schematic diagram of another embodiment which is similar to that discussed above with respect to FIG. 9, but with the addition of an adaptive optical element 92 in replacement of scanning mirrors 56/58 in scanning assembly 48, for scanning the light 46. In this embodiment, adaptive optical element 92 may be reconfigured to produce a complex optical system. For example, both a scan and any possible anamorphic correction maybe made to light 46 with this single element. Some examples of such an optical element 92 include: deformable mirrors, deformable lenses, and optical phase arrays.

Figure 16:
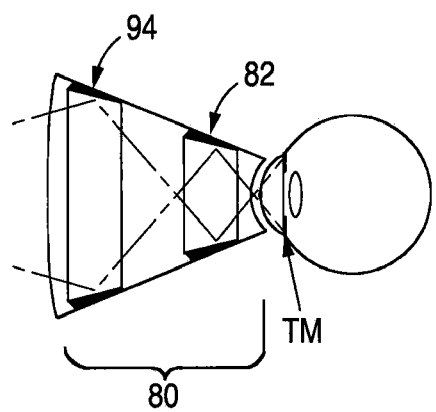
FIG. 16 is a side cross-sectional view of another alternate embodiment of the gonioscopic lens assembly of the present invention, optimized for scanning therapy.

FIG. 16 shows another aspect of the present invention, in which an additional internal mirror 94 is added to the lens assembly 80 of FIG. 12. Internal mirror 94 works in cooperation with gonioscopic mirror 82 to produce an erect image of the trabecular meshwork TM. Both internal mirror 94 and gonioscopic mirror 82 may independently include single or multiple facets, or a single continuous element, as discussed in the description of FIGS. 11-12.

Figure 17:
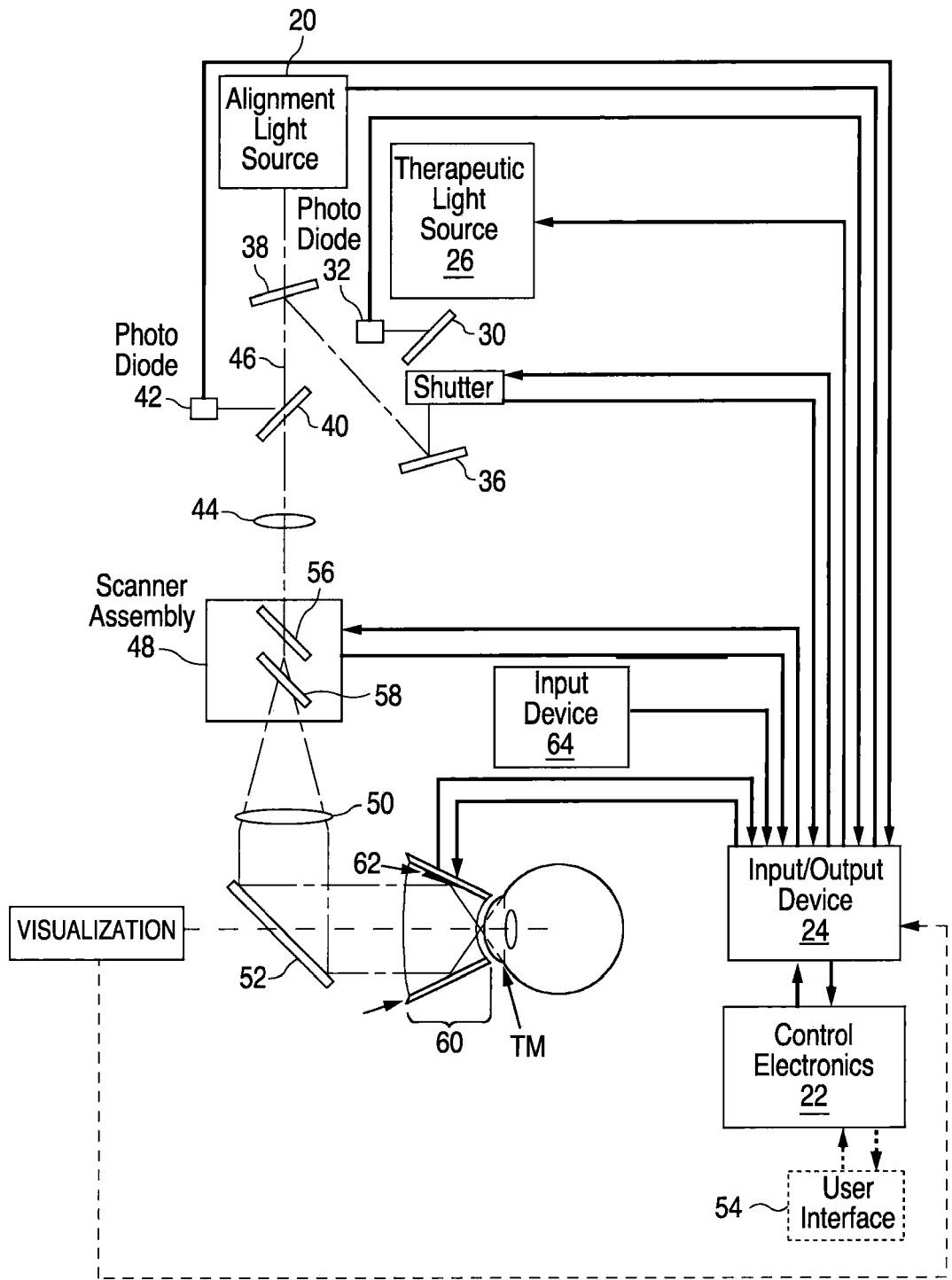
FIG. 17 is a schematic diagram illustrating yet another alternate embodiment of the light generation and scanner assembly of the present invention.

FIG. 17 shows another aspect of the present invention, in which the gonioscopic mirror 62 within the contact lens is made to rotate in conjunction with the output of the scanner to allow for a complete 360 degree treatment of the TM without the complication of anamorphic correction. Gonioscopic mirror 62 may be mounted on to the inner surface of the lens assembly housing, and made to rotate about the lens'optical axis in a manner that keeps constant angle between the face of the mirror and the optical axis of the incoming beam. This may be done in a number of different ways, such as by use of a small motor and an external contact spur gear assembly to directly rotate the mirror housing, or a rack and pinion with a helical cam and follower arrangement. Furthermore, the use of a rotary encoder to monitor the lens'position would allow for its safe use in a closed-loop feedback system.

It is to be understood that the present invention is not limited to the embodiment(s) described above and illustrated herein, but encompasses any and all variations falling within the scope of the appended claims. For example, the scanning method and apparatus of the present invention can be directed to ophthalmic tissues other than TM. In addition, the alignment pattern and light source could be omitted where the therapeutic pattern can be manually aimed by use of other optical elements in the optical path.

What is claimed is:

1. An optical scanning system for performing therapy on target eye tissue of a patient, comprising:
    a light source for producing a beam of light;
    a scanning device that includes at least one movable optical element for moving the beam of light to produce a pattern of the light beam;
    a controller for controlling the scanning device to create the light beam pattern in response to a user command from an input device;
    at least one lens for focusing the pattern of the light beam from the scanning device in a telecentric manner; and
    an ophthalmic lens assembly having a contact surface for contacting the patient and having a reflective optical element for reflecting the light beam pattern from the at least one lens onto the target eye tissue;
    wherein the at least one lens is configured such that the telecentric focusing of the pattern is parallel to an optical axis of the ophthalmic lens assembly before reaching the ophthalmic lens assembly.

2. The optical scanning system of claim 1, wherein light emanates from the target eye tissue, and wherein the system further comprises:
    a second optical element for reflecting the light beam pattern from the scanning device or from the at least one lens to the ophthalmic lens assembly, and for transmitting a portion of the light emanating from the target eye tissue to provide visualization of the light beam pattern on the target eye tissue.

3. The optical scanning system of claim 1, wherein the light beam pattern includes at least two spots that do not completely overlap each other.

4. The optical scanning system of claim 3, wherein the light source includes a pulsed light source component.

5. The optical scanning system of claim 1, wherein the light beam pattern includes a line segment.

6. The optical scanning system of claim 5, wherein the light source includes a continuous wave light source component.

7. The optical scanning system of claim 1, wherein the reflective optical element comprises a plurality of mirror facets abutted together to form a continuous annular mirror, and wherein the light beam pattern is reflected by the mirror facets.

8. The optical scanning system of claim 1, wherein the reflective optical element comprises a continuously formed annular mirror providing a continuous 360 degree view of the target eye tissue, and wherein the light beam pattern is reflected by the annular mirror.

9. The optical scanning system of claim 1, wherein the light source produces alignment light and therapeutic light in the light beam.

10. The optical scanning system of claim 9, wherein the light source includes a first light producing device for producing the alignment light and a second light producing device separate from the first light producing device for producing the therapeutic light.

11. The optical scanning system of claim 9, wherein the light beam pattern includes an alignment pattern of the alignment light and a therapeutic pattern of the therapeutic light.

12. The optical scanning system of claim 11, wherein the alignment pattern provides a visual indication of a location of the therapeutic pattern on the target eye tissue.

13. The optical scanning system of claim 11, wherein the alignment light is visual light, and the therapeutic light is non-visible light.

14. The optical scanning system of claim 11, wherein the alignment light has a lower power than that of the therapeutic light.

15. The optical scanning system of claim 1, wherein the target eye tissue is trabecular meshwork of the patient's eye, and wherein the reflective optical element is a gonioscopic mirror mounted in the ophthalmic lens assembly.

16. The optical scanning system of claim 1, wherein the controller is configured for controlling the scanning device and the reflective optical element such that the reflective optical element moves in coordination with the movement of the beam.

17. The optical system of claim 1, wherein the at least one lens is disposed one focal length of the at least one lens away from the scanning device.

18. The optical system of claim 1, wherein:
    the scanning device includes a pair of movable optical elements for the moving of the beam of the light, and
    the at least one lens is disposed one focal length of the at least one lens away from an optical midpoint of the pair of movable optical elements.

19. An optical scanning system for performing therapy on trabecular meshwork of a patient's eye, comprising:
    a light source for producing a beam of light;
    a scanning device that includes at least one movable optical element for moving the beam of light to produce a pattern of the light beam; and
    a controller for controlling the scanning device to create the light beam pattern in response to a user command from an input device;
    at least one lens for focusing the pattern of the light beam from the scanning device in a telecentric manner; and
    an ophthalmic lens assembly for placement over a patient's eye and including a reflective optical element for reflecting the light pattern from the at least one lens onto the trabecular meshwork of the patient's eye;
    wherein the at least one lens is configured such that the telecentric focusing of the pattern is parallel to an optical axis of the ophthalmic lens assembly before reaching the ophthalmic lens assembly.

20. The optical scanning system of claim 19, wherein the controller is configured for controlling the scanning device and the ophthalmic lens assembly such that the reflective optical element moves in coordination with the movement of the beam.

21. The optical scanning system of claim 19, wherein the light beam pattern includes at least two spots that do not completely overlap each other.

22. The optical scanning system of claim 21, wherein the light source includes a pulsed light source component.

23. The optical scanning system of claim 19, wherein the light beam pattern includes a line segment.

24. The optical scanning system of claim 23, wherein the light source includes a continuous wave light source component.

25. The optical scanning system of claim 19, wherein the reflective optical element comprises a plurality of mirror facets abutted together to form a continuous annular mirror.

26. The optical scanning system of claim 19, wherein the reflective optical element comprises a continuously formed annular mirror providing a continuous 360 degree view of the trabecular meshwork of the patient's eye.

27. The optical scanning system of claim 19, wherein the light source produces alignment light and therapeutic light in the light beam.

28. The optical scanning system of claim 27, wherein the light source includes a first light producing device for producing the alignment light and a second light producing device separate from the first light producing device for producing the therapeutic light.

29. The optical scanning system of claim 27, wherein the light beam pattern includes an alignment pattern of the alignment light and a therapeutic pattern of the therapeutic light.

30. The optical scanning system of claim 29, wherein the alignment pattern provides a visual indication of a location of the therapeutic pattern on the trabecular meshwork of the patient's eye.

31. The optical scanning system of claim 27, wherein the alignment light is visual light, and the therapeutic light is non-visible light.

32. The optical scanning system of claim 27, wherein the alignment light has a lower power than that of the therapeutic light.

33. The optical system of claim 19, wherein the at least one lens is disposed one focal length of the at least one lens away from the scanning device.

34. The optical system of claim 19, wherein:
the scanning device includes a pair of movable optical elements for the moving of the beam of the light, and
the at least one lens is disposed one focal length of the at least one lens away from an optical midpoint of the pair of movable optical elements.

35. A method of performing therapy on trabecular meshwork of a patient's eye, comprising:
placing an ophthalmic lens assembly over the patient's eye, wherein the ophthalmic lens assembly includes a reflective optical element;
producing a beam of light;
moving the beam of light to produce a pattern of the light beam using a scanning device that includes at least one movable optical element and is under the control of a controller;
focusing the pattern of the light beam in a telecentric manner parallel to an optical axis of the eye using at least one lens; and
reflecting the telecentrically focused light pattern off of the reflective optical element and onto the trabecular meshwork of the patient's eye.

36. The method of claim 35, further comprising:
moving the reflective optical element in coordination with the moving of the light beam.

37. The method of claim 35, wherein the moving of the light beam is performed such that the light beam pattern includes at least two spots that do not completely overlap each other.

38. The method of claim 37, wherein the producing of the light beam includes producing pulsed light in the light beam.

39. The method of claim 35, wherein the moving of the light beam is performed such that the light beam pattern includes a line segment.

40. The method of claim 39, wherein the producing of the light beam includes producing continuous wave light in the light beam.

41. The method of claim 35, wherein the reflective optical element comprises a plurality of mirror facets abutted together to form a continuous annular mirror.

42. The method of claim 35, wherein the reflective optical element comprises a continuously formed annular mirror providing a continuous 360 degree view of the trabecular meshwork of the patient's eye.

43. The method of claim 35, wherein the producing of the light beam includes producing alignment light and therapeutic light in the light beam.

44. The method of claim 43, wherein the light beam pattern includes an alignment pattern of the alignment light and a therapeutic pattern of the therapeutic light.

45. The method of claim 44, further comprising:
viewing the alignment pattern on the trabecular meshwork of the patient's eye, wherein the alignment pattern provides a visual indication of a location of the therapeutic pattern on the trabecular meshwork of the patient's eye.

46. The method of claim 44, wherein the alignment light is visual light, and the therapeutic light is non-visible light.

47. The method of claim 44, wherein the alignment light has a lower power than that of the therapeutic light.

48. The method of claim 35, further comprising:
activating an input device of the controller, wherein the controller causes the scanning device to move the beam and produce the light pattern in response to the input device activation.

49. The method of claim 35, wherein the at least one lens is disposed one focal length of the at least one lens away from the scanning device.

50. The method of claim 35, wherein:
the scanning device includes a pair of movable optical elements for the moving of the beam of light, and
the at least one lens is disposed one focal length of the at least one lens away from an optical midpoint of the pair of movable optical elements.

* * * * *